United States Patent [19]
Kalindjian et al.

[11] Patent Number: 5,939,437
[45] Date of Patent: Aug. 17, 1999

[54] CCK AND GASTRIN RECEPTOR LIGANDS

[75] Inventors: Sarkis Barret Kalindjian, Banstead; Katherine Isobel Mary Steel, Beckenham; David John Dunstone; Ildiko Maria Buck, both of London, all of United Kingdom

[73] Assignee: James Black Foundation Limited, London, United Kingdom

[21] Appl. No.: 08/737,317

[22] PCT Filed: May 2, 1995

[86] PCT No.: PCT/GB95/00997

§ 371 Date: Dec. 20, 1996

§ 102(e) Date: Dec. 20, 1996

[87] PCT Pub. No.: WO95/30647

PCT Pub. Date: Nov. 16, 1995

[30] Foreign Application Priority Data

May 9, 1994 [GB] United Kingdom .................. 9409150

[51] Int. Cl.$^6$ ...................... C07C 237/22; A61K 31/165; C07D 213/82; C07D 307/68
[52] U.S. Cl. .......................... 514/330; 514/212; 514/423; 514/616; 564/153; 548/540; 546/226; 540/607
[58] Field of Search ............................ 564/153; 514/616, 514/212, 330, 423; 540/607; 546/226; 548/540

[56] References Cited

FOREIGN PATENT DOCUMENTS 0 336 356   10/1989   European Pat. Off. .
93 16982    9/1993    WIPO .

OTHER PUBLICATIONS

Endres, W. (Arch. Pharm. (Weinheim), 308 (8), 571–579, 1972.
Nilsson, "Gastrin: Isolation, Characterization, and Functions", Gastrointestinal Hormones, (1980).
Mutt, "Cholecystokinin: Isolation, Structure, and Functions", Gastrointestinal Hormones, (1980).
Stella et al., "Prodrugs: Do They Have Advantages in Clinical Practice", Drugs, vol. 29, (1985), pp. 455–473.
Gross, "The Peptides: Analysis, Synthesis, Biology", Major Methods of Peptide Bond Formation, vol. 1, (1979).
Rich et al., "The Carbodiimide Method", The Peptides, vol. 1, (1979).

*Primary Examiner*—Mukund J. Shah
*Assistant Examiner*—Bruck Kifle
*Attorney, Agent, or Firm*—Foley & Lardner

[57] ABSTRACT

Compounds of formula (I) and their pharmaceutically active salts are gastrin and CCK receptor ligands, where Ar is a monocyclic aromatic group, $R^1$ is halo, amino, nitro, cyano, sulphamoyl, sulphonyl, trifluoromethyl, $C_1$ to $C_3$ alkyl, $C_1$ to $C_3$ alkylamino, $C_1$ to $C_3$ dialkylamino, phenyl, substituted phenyl, $C_1$ to $C_3$ alkoxy, hydroxy, esterified hydroxy, $C_1$ to $C_3$ hydroxyalkyl, $C_1$ to $C_3$ alkylcarboxyamino, carboxy, esterified carboxy and amidated carboxy, m is 0, 1, 2, 3, or 4, provided that m is not more than 2 unless $R^1$ is exclusively halo, x+y=0 or 1, $R^2$ and $R^4$ independently are H, or $C_1$ to $C_3$ alkyl, $R^3$ is H or $C_1$ to $C_{15}$ hydrocarbyl, where one or more hydrogen atoms of die hydrocarbyl group may be replaced by a halogen atom, and where up to two of the carbon atoms may be replaced by a nitrogen, oxygen or sulphur atom, provided that $R^3$ does not contain a —O—O— group, $R^5$ is H or $C_1$ to $C_3$ alkyl, U is a cyclic moiety, selected from the group consisting of aryl, aromatic heterocyclic, non-aromatic heterocyclic, and cycloalkyl groups, where the aryl or aromatic group contains up to 3 substituents selected from the group consisting of halo, amino, nitro, cyano, sulphamoyl, sulphonyl, trifluoromethyl, $C_1$ to $C_3$ alkyl, $C_1$ to $C_3$ alkylamino, $C_1$ to $C_3$ dialkylamino, phenyl, $C_1$ to $C_3$ alkoxy, hydroxy, esterified hydroxy, $C_1$ to $C_3$ hydroxyalkyl, $C_1$ to $C_3$ alkylcarboxyamino, carboxy, esterified carboxy and amidated carboxy, Z is a group of the formula (IIa) or (IIb) where $R^6$ is H or $C_1$ to $C_3$ alkyl, X is —$CO_2H$, esterified carboxy, amidated carboxy, tetrazolyl, hydroxy, cyano, amidino, —$CH_2OH$, —$SO_2NHCOR^7$, —$SONHCOR^7$, —$COR^7$, —$NHSO_2R^7$, —$CONHSO_2R^7$,— $NHCOR^7$ or —$SO_2NHR^8$, where $R^7$ is $C_1$ to $C_6$ alkyl, $C_1$ to $C_6$ aryl or substituted aryl, and $R^8$ is —OH, —CN, $C_1$ to $C_6$ alkyl, $C_1$ to $C_6$ haloalkyl, aryl or substituted aryl, Y is H or a group selected from those recited above for X, and a is 0, 1, or 2.

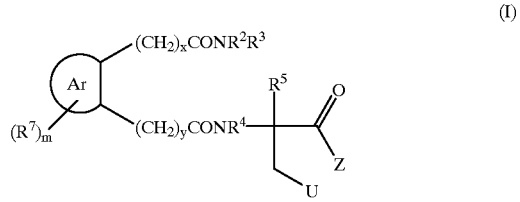

(I)

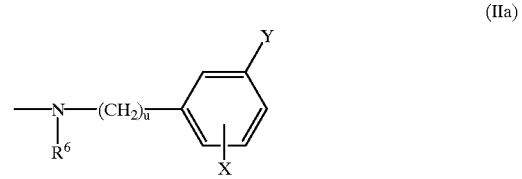

(IIa)

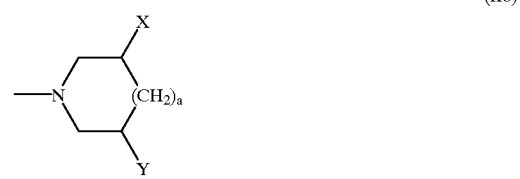

(IIb)

6 Claims, No Drawings

CCK AND GASTRIN RECEPTOR LIGANDS

This invention relates to compounds which bind to cholecystokinin and/or gastrin receptors. The invention also relates to methods for preparing such compounds.

Gastrin and the CCK's are structurally-related neuropeptides which exist in gastrointestinal tissue and in the CNS (see Mutt V., *Gastrointestinal Hormones*, Glass G. B. J., ed., Raven Press, New York, p 169 and Nisson G., ibid, p. 127).

Gastrin is one of the three primary stimulants of gastric acid secretion. Several forms of gastrin are found including 34-, 17-, and 14-amino acid species with the minimum active fragment being the C-terminal tetrapeptide (TrpMetAspPhe-$NH_2$) which is reported in the literature to have full pharmacological activity (see Tracey H. J. and Gregory R. A., Nature (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal motility, gall bladder contraction, pancreatic enzyme secretion, and are known to have a trophic action on the pancreas. They also inhibit gastric emptying and have various effects in the CNS.

Compounds which bind to cholecystokinin and/or gastrin receptors are important because of their potential pharmaceutical use as antagonists of the natural peptides.

A number of gastrin antagonists have been proposed for various therapeutic applications, including the prevention of gastrin-related disorders, gastrointestinal ulcers, Zollinger-Ellison syndrome, antral G Cell hyperplasia and other conditions in which lowered gastrin activity is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatment of cancers, especially of the pancreas. Moreover, ligands for cholecystokinin receptors in the brain (so-called $CCK_B$ receptors) have been claimed to possess anxiolytic activity.

According to the present invention, there are provided compounds of the formula

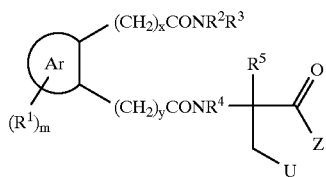

(I)

wherein
Ar is a monocyclic aromatic group,
$R^1$ (or each $R^1$ group, when m is 2 or more) is selected from halo, amino, nitro, cyano, sulphamoyl, sulphonyl, trifluoromethyl, $C_1$ to $C_3$ alkyl, $C_1$ to $C_3$ alkylamino, $C_1$ to $C_3$ dialkylamino, phenyl, substituted phenyl, $C_1$ to $C_3$ alkoxy, hydroxy, esterified hydroxy, $C_1$ to $C_3$ hydroxyalkyl, $C_1$ to $C_3$ alkylcarboxyamino, carboxy, esterified carboxy and amidated carboxy m is from 0 to 4, provided that m is not more than 2 unless $R^1$ is exclusively halo, x+y=0 or 1

$R^2$ and $R^4$ are independently H, $C_1$ to $C_3$ alkyl or a $C_1$ to $C_3$ alkylene link to an ortho carbon atom in the aromatic ring, $R^3$ is H or $C_1$ to $C_{15}$ hydrocarbyl, in which one or more hydrogen atoms of the hydrocarbyl group may be replaced by a halogen atom, and up to two of the carbon atoms may be replaced by a nitrogen, oxygen or sulphur atom, provided that $R^3$ does not contain a —O—O— group, $R^5$ is H or $C_1$ to $C_3$ alkyl, U is aryl, substituted aryl, heterocyclic, substituted heterocyclic or cycloalkyl, and Z is a group of the formula

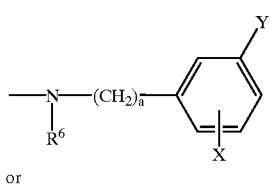

(II)

or

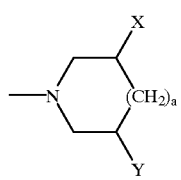

(wherein $R^6$ is H or $C_1$ to $C_3$ alkyl,

X is —$CO_2H$, esterified carboxy, amidated carboxy, tetrazolyl, hydroxy, cyano, amidino, —$CH_2OH$, —$SO_2NHCOR^7$, —$SONHCOR^7$, —$COR^7$, —$NHSO_2R^7$, —$CONHSO_2R^7$, —$NHCOR^7$ or —$SO_2NHR^8$, in which $R^7$ is alkyl (eg $C_1$ to $C_6$ alkyl), haloalkyl (eg $C_1$ to $C_6$ haloalkyl), aryl or substituted aryl, and $R^8$ is —OH, —CN, or a group selected from those recited above for $R^7$, Y is H or a group selected from those recited above for X, and a is from 0 to 2)

and pharmaceutically acceptable salts thereof.

Included within the present invention are compounds ("pro-drugs") which are degraded in vivo to yield the desired pharmacologically active species. Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al, "Prodrugs", *Drug Delivery Systems*, pp. 112–176 (1985), and *Drugs*, 29, pp.455–473 (1985).

Pro-drug forms of the pharmacologically-active compounds of the invention will generally be compounds according to formula (I) in which X and/or Y represents an esterified or amidated acid group. Included in such esterified acid groups are groups of the form —COOR$^9$, wherein R$^9$ is C$_1$ to C$_5$ alkyl, phenyl, substituted phenyl, benzyl, substituted benzyl, indanolyl or one of the following:

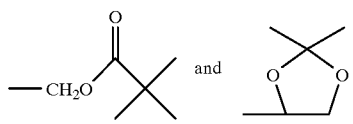

(III)

Amidated acid groups include groups of the formula —CONR$^{10}$R$^{11}$, wherein R$^{10}$ is H, C$_1$ to C$_5$ alkyl, phenyl, substituted phenyl, benzyl, or substituted benzyl and R$^{11}$ is —OH or one of the groups just recited for R$^{10}$.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups, A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

A "heterocyclic" group comprises one or more closed chains or rings which have at least one atom other than carbon in the closed chain or ring. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

Ar is preferably a five- or six-membered ring having no more than two heteroatoms, and more preferably is selected from the monocyclic aromatic groups (whether carbocyclic or heterocyclic) specifically mentioned above.

The term "halogen", as used herein, refers to any of fluorine, chlorine, bromine and iodine. Most usually, however, halogen substituents in the compounds of the invention are chlorine or fluorine substituents.

When m is not 0, R$^1$ is preferably selected from halo, hydroxy, amino, nitro, cyano, sulphamoyl, C$_1$ to C$_3$ alkyl and C$_1$ to C$_3$ alkoxy. As mentioned above, when m is 2, each R$^1$ group is independent of the other. That is, the compounds of the invention may include two different R$^1$ groups.

When reference is made herein to a "substituted" aromatic group, the substituents will generally be from 1 to 3 in number (and more usually 1 or 2 in number), and selected from the groups recited above for R$^1$, provided that such substituents are not themselves substituted aromatic groups.

Preferably, R$^3$ is C$_6$ to C$_8$ straight or branched chain alkyl or cycloalkyl, or R$^{12}$—(CH$_2$)$_p$—, wherein R$^{12}$ is selected from phenyl, 1-naphthyl, 2-naphthyl, indolyl, norbornyl, 1-adamantyl, 2-adamantyl, cyclohexyl or cycloheptyl, and p is from 0 to 3.

The group X is preferably —CO$_2$H or tetrazolyl, and Y is preferably H, —CO$_2$H or tetrazolyl.

When R$^2$ or R$^4$ is an alkylene link to the aromatic ring, the compounds of the invention take the form

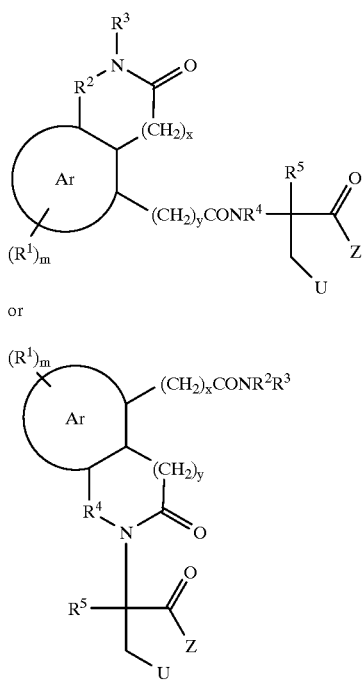

Pharmaceutically acceptable salts of the acidic compounds of the invention include salts with alkali metals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, phosphoric acid, oxalic acid, maleic acid, succinic acid and citric acid.

The compounds of the invention may exist in various regioisomeric, enantiomeric and diastereomeric forms. It will be understood that the invention comprehends the different regioisomers, enantiomers and diastereomers in isolation from each other, as well as mixtures of regioisomers, enantiomers and diastereomers.

Compounds according to the present invention may conveniently be made by the process depicted in Reaction Scheme A.

Reaction Scheme A

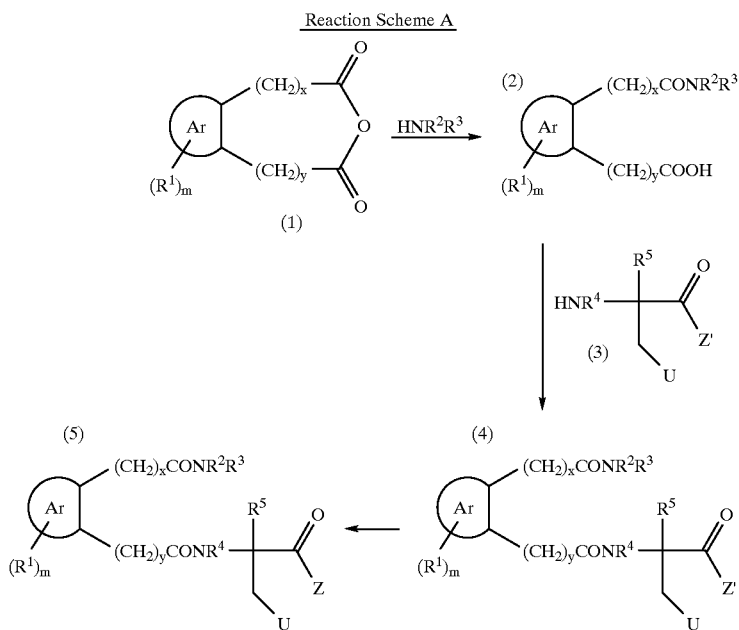

In Reaction Scheme A, the acid anhydride (1) is reacted with an amine of the formula HNR²R³. The resulting acid compound (2) is then amidated with compound (3), Z' representing a group of formula (II) above, in which the acid substituents X and Y have been suitably protected. Conventional deprotection of the resulting compound (4) yields the desired end product (5).

Suitable amidation methods are described in detail in "The Peptides, Vol. 1", Gross and Meinenhofer, Eds., Academic Press, New York, 1979. These include the carbodiimide method (using, for example, 1,3-dicyclohexylcarbodiimide [DCC] or 1-(3-dimethylaminopropyl)-3-ethylcarbodiimide hydrochloride [EDCI], and optionally an additive such as 1-hydroxybenzotriazole [HOBT] to prevent racemization), the azide method, the mixed anhydride method, the symmetrical anhydride method, the acid chloride method, the use of bis (2-oxo-3-oxazolidinyl) phosphinic chloride [BOP-Cl], the use of PyBOP or PyBrOP, the use of the isopropenylsuccinimido carbonate method and the active ester method (using, for example, N-hydroxysuccinimide esters, 4-nitrophenyl esters or 2,4,5-trichlorophenol esters).

The coupling reactions are generally conducted under an inert atmosphere, such as an atmosphere of nitrogen or argon. Suitable solvents for the reactants include methylene chloride, tetrahydrofuran [THF], dimethoxyethane [DME] and dimethylformamide [DMF].

The invention therefore also provides a method of making a compound according to formula (I) above, said method including the step of reacting a compound of the formula

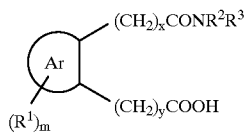

with a suitably protected compound of formula

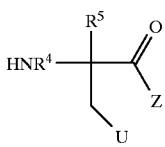

In some cases, it may be appropriate to carry out the amidation reactions in a different order. The invention therefore also comprehends a method of making a compound according to formula (III) above, said method including the step of reacting a compound of the formula

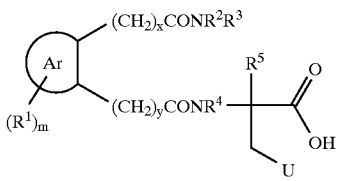

with a suitably protected compound of formula

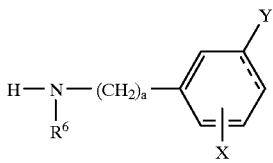

or

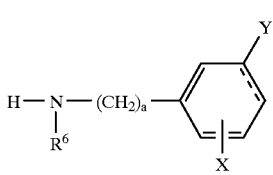

-continued

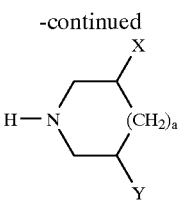

or reacting a compound of the formula

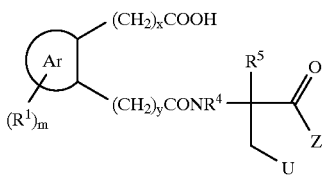

with a suitably protected compound of formula $HNR^2R^3$.

Pharmaceutically acceptable salts of the acidic or basic compounds of the invention can of course made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated and the weight of the patient. In general, however, the daily dose (whether administered as a single dose or as divided doses) will be in the range 0.001 to 5000 mg per day, and more usually from 1 to 1000 mg per day. Expressed as dosage per unit body weight, a typical dose will be between 0.01 μg/kg and 50mg/kg, eg between 10 μg/kg and 10 mg/kg.

The invention is now further illustrated by means of the following examples.

EXAMPLE 1

Preparation of (1S-(3,5-dicarboxyphenylaminocarbonyl)-2-phenylethylaminocarbonyl)-2-(1-adamantanemethylaminocarbonyl)-benzene a. 3,5-dibenzyloxycarbonylnitrobenzene 5-nitro-isophthalic acid (21.1 g, 0.1 mol), thionyl chloride (80 ml) and DMF (10 drops) were stirred and heated for about 1 h until a clear solution was obtained. Excess thionyl chloride was removed by evaporation and the residual acid chloride was coevaporated with dichloromethane (2×100 ml) to remove the last traces.

Benzyl alcohol (21.6 g, 0.2 mol) and triethylamine (30.03 g, 0.3 mol) were dissolved in dichloromethane (200 ml) and stirred at 0° under an atmosphere of dry nitrogen and a solution of the acid chloride in dichloromethane (50 ml) was added dropwise over 20 min. The solution was stirred and refluxed for 1 h, and the solution was cooled. The organic layer was washed with water (2×100 ml), saturated sodium hydrogencarbonate solution (100 ml) and dried over magnesium sulphate. The solution was filtered and evaporated to leave the title compound (39.1 g, 100%), $^1$H NMR (CDCl$^3$) δ9.0 (3H, d), 7.5 (10H, m), 5.5 (4H, s).

b. 3,5-dibenzyloxycarbonylaniline 3,5-dibenzyloxycarbonylnitrobenzene (3.91 g, 10 mol) was dissolved in ethyl acetate (50 ml) and tin(II)chloride dihydrate (11.27 g, 50 mmol) was added and the mixture stirred and heated at 70° under an atmosphere of nitrogen for 1 h. The mixture was poured carefully onto 5% sodium hydrogencarbonate solution (200 ml) and a further aliquot of ethyl acetate (100 ml) was added. After shaking the organic layer was separated and the aqueous layer was extracted with more ethyl acetate (50 ml). The combined organic layers were washed with brine, and dried, filtered and evaporated to leave a pale yellow solid (3.25 g, 90%), $^1$H NMR (CDCl$_3$) δ 8.1 (1H, d), 7.5 (12H, m), 5.4 (4H, s), 3.8 (2H, bs).

c. N-tert-butyloxycarbonyl-1S-(3,5-dibenzyloxycarbonylphenylamino-carbonyl)-2-phenylethylamine BOC-L-phenylalanine (8.76 g, 33 mmol) was dissolved in dry dichloromethane (200 ml) and dry diisopropylethylamine (11.48 ml, 66 mmol) was added followed by PyBROP (15.33 g, 33 mol). The mixture was stirred at room temperature for 5 min and then 3,5-dibenzyloxycarbonylaniline (7.22 g, 20 mmol) was added. The solution was stirred at room temperature for a further 5 h and the solution was then washed sequentially with 2M hydrochloric acid, water, saturated sodium hydrogencarbonate solution and water and finally dried, filtered and evaporated to leave an oil. This was purified by column chromatography (90% dichloromethane and 10% ethyl acetate) to leave the title compound as a white solid (11.0 g, 90%). $^1$H NMR (d$^6$-DMSO) δ 10.5 (1H, s), 8.5 (2H, s), 8.2 (1H, s), 7.3 (15H, m), 5.4 (4H, s), 4.3 (1H, m), 2.9 (2H, m), 1.3 (9H,s)

d. 1S-(3,5-dibenzyloxycarbonylphenylaminocarbonyl)-2-phenyl-ethylamine

N-tert-butyloxycarbonyl-1S-(3,5-dibenzyloxycarbonylphenyl-aminocarbonyl)-2- phenylethylamine (8.0 g, 13 mmol) was dissolved in trifluoroacetic acid (40 ml) and stirred at room temperature for 30 min. The solvent was removed by evaporation and the residue taken up in dry dichloromethane (50 ml) and washed with saturated sodium hydrogencarbonate (3×30ml), water (30ml) and brine (30ml). The solution was dried over anhydrous sodium sulphate, filtered and evaporated to give the title compound (6.5g, 98%). $^1$H NMR (d$^6$-DMSO) δ 8.5 (2H, s), 8.2 (1H, s), 7.3 (14H, m), 5.4 (4H, s), 3.6 (1H, m), 2.9 (1H, m), (2.8 (1H,m).

e. 2-(1-adamantylmethylaminocarbonyl)benzoic acid

Phthalic anhydride (2.65 g, 17.9 mmol) was dissolved in dry THF (50 ml) and a solution of 1-adamantanemethylamine (2.96 g, 17.9 mmol) in THF (50 ml) was added. The mixture was stirred at room temperature for 16 h and the solution evaporated to dryness. The residue was triturated with hexane and the precipitate formed was filtered, washed with hexane and dried to leave the title compound (5.42 g, 97%), $^1$H NMR (d$^6$-DMSO) δ 12.9 (1H, s), 8.2 (1H, t), 7.8–7.4 (4H, m), 2.9 (2H, d), 1.9 (3H, s), 1.6 (6H, q), 1.5 (6H, s).

f. (1S-(3,5-dibenzyloxycarbonylphenylaminocarbonyl)-2-phenyl-ethylaminocarbonyl)-2-(1-adamantanemethylaminocarbonyl)benzene 2-(1-adamantanemethylaminocarbonyl)benzoic acid (step e above) (500 mg, 1.59 mmol), 1S-(3,5-dibenzyloxycarbonylphenylaminocarbonyl)-2-phenylethylamine (step d above) (811 mg, 1.59 mmol) and PyBROP (744 mg, 1.59 mmol) were taken up in dry dichloromethane (50 ml) and Hunigs base (0.42 ml, 2.4 mmole) was added. A catalytic quantity of DMAP (10 mg) was introduced and the reaction mixture was stirred under an atmosphere of dry argon at room temperature for 3 h. The organic layer was washed with 2M hydrochloric acid (3×20 ml) and then dried, filtered and evaporated to leave the crude title compound which was further purified by column chromatography (silica, 10% ethyl acetate and 90% dichloromethane). The title compound (816 mg, 64%) was isolated as a white solid, $^1$H NMR (d$^6$-DMSO) δ 10.3 (1H, s), 8.9 (1H, d), 8.8 (2H, d), 8.5 (1H, t), 8.3 (1H, t), 7.7–7.0 (19H, m), 5.4 (4H, q), 4.7 (1H, m), 3.4–2.8 (4H, m), 2.0–1.3 (15H, m).

g. (1S-(3,5-dicarboxyphenylaminocarbonyl)-2-phenylethylamino-carbonyl)-2-(1-adamantanemethylaminocarbonyl)benzene (1S-(3,5-dibenzyloxycarbonylphenylaminocarbonyl)-2-phenyl-ethylaminocarbonyl)-2-(1-adamantanemethylaminocarbonyl)benzene (product of step f) (816 mg, 1.0 mmol) was dissolved in a 1:1 mixture of methanol and THF (50 ml). 10% Palladium-on-charcoal (80 mg) was added and the mixture was stirred under an atmosphere of hydrogen gas for 16 h. The solution was filtered through a pad of celite and then evaporated to dryness to leave the title compound as a colourless solid (428 mg, 68%), $^1$H NMR (d6-DMSO) δ 10.2 (1H, s), 8.9 (1H, d), 8.7 (2H, d), 8.5 (1H, t), 8.2 (1H, s), 7.7–6.9 (9H, m), 4.7 (1H, m), 3.6–2.9 (4H, m), 1.9–1.3 (15H, m).

The compound was further characterised and tested as the di-N-methyl-D-glucamine salt found: C, 57.38; H, 7.22; N, 6.59. $C_{50}H_{71}N_5O_{17}$. 1.8 $H_2O$ requires C, 57.36; H, 7.19; N, 6.59%

EXAMPLE 2

Preparation of (1S-(3,5-dicarboxyphenylaminocarbonyl)-2-(4-hydroxyphenyl)-ethylaminocarbonyl)-2-(1-adamantanemethyl-aminocarbonyl)-benzene The material was prepared essentially as in example 1 except that BOC-L-tyrosine was used in step c instead of BOC-L-phenylalanine. $^1$H NMR (d$^6$-DMSO) δ 13.2 (2H, s), 10.2 (1H, s), 9.3 (1H, s), 8.9 (1H, d), 8.7 (2H, s), 8.5 (1H, t), 8.2 (1H, s), 7.6 (1H, m), 7.5 (2H, m), 7.1 (2H, d), 7.0 (1H, m), 6.7 (2H, d), 4.7 (1H, m), 3.6–2.9 (4H, m), 1.9 (3H, s), 1.5 (6H, q), 1.3 (6H, s).

The compound was further characterised and tested as the di-N-methyl-D-glucamine salt found: C, 54.99; H, 6.98; N, 6.51. $C_{50}H_{71}N_5O_{18}$. 3.2 $H_2O$ requires C, 57.18; H, 7.17; N, 6.51%

EXAMPLE 3

Preparation of (1R-(3,5-dicarboxyphenylaminocarbonyl)-2-phenylethylaminocarbonyl)-2-(1-adamantanemethylaminocarbonyl)-benzene The material was prepared essentially as in example 1 except that BOC-D-phenylalanine was used in step c instead of BOC-L-phenylalanine. $^1$H NMR (d$^6$-DMSO) δ 10.2 (1H, s), 8.9 (1H, d), 8.7 (2H, d), 8.5 (1H, t), 8.2 (1H, s), 7.7–6.9 (9H, m), 4.7 (1H, m), 3.6–2.9 (4H, m), 1.9–1.3 (15H, m).

The compound was further characterised and tested as the di-N-methyl-D-glucamine salt found: C, 56.14; H, 7.18; N, 6.41. $C_{50}H_{71}N_5O_{17}$. 3.2 $H_2O$ requires C, 56.08; H, 7.28; N, 6.54%

EXAMPLE 4

Preparation of (1R-(3,5-dicarboxyphenylaminocarbonyl)-2-2-fluorophenyl)ethylaminocarbonyl)-2-(1-adamantanemethylamino-carbonyl)benzene The material was prepared essentially as in example 1 except that BOC-L-2-fluorophenylalanine was used in step c instead of BOC-L-phenylalanine. $^1$H NMR (d$^6$-DMSO) δ 13.2 (2H, br s), 10.1 (1H, s), 8.9 (1H, d), 8.7 (2H, d), 8.5 (1H, t), 8.2 (1H, t), 7.7–6.9 (8H, m), 4.8 (1H, m), 3.6–2.9 (4H, m), 1.9–1.3 (15H, m).

The compound was further characterised and tested as the di-N-ethyl-D-glucamine salt found: C, 56.79; H, 7.18; N, 6.69. $C_{50}H_{70}FN_5O_{17}$. 1.5 $H_2O$ requires C, 56.66; H, 6.95; N, 6.61%

EXAMPLE 5

Preparation of (1R-(3,5-dicarboxyphenylaminocarbonyl)-2-phenylethylaminocarbonyl)-2-(1-naphthalenemethylaminocarbonyl)-benzene The material was prepared essentially as in example 1 except that 1-naphthalenemethylamine was used in step e instead of 1-adamantanemethylamine. $^1$H NMR (d$^6$-DMSO) δ 10.2 (1H, s), 9.2 (1H, m), 8.9 (1H, m), 8.6 (2H, s), 8.0 (1H, s), 8.0–7.0 (16H, m), 5.0 (1H, m), 4.9 (1H,m), 4.8 (1H,m), 3.5–2.8 (2H, m).

The compound was further characterised and tested as the di-N-methyl-D-glucamine salt found: C, 57.19; H, 6.51; N, 6.57. $C_{50}H_{63}N_5O_{17}$. 2.5$H_2O$ requires C, 57.11; H, 6.52; N, 6.66%

EXAMPLE 6

Preparation of (1R-(3,5-dicarboxyphenylaminocarbonyl)-2-phenylethylaminocarbonyl)-2-(2-naphthalenemethylaminocarbonyl)-benzene The material was prepared essentially as in example 1 except that 2-naphthalenemethylamine was used in step e instead of 1-adamantanemethylamine and that Adams catalyst was used in step g instead of palladium-on-charcoal. $^1$H NMR (d$^6$-DMSO) δ 10.1 (1H, s), 9.3 (1H, t), 8.9 (1H, d), 8.6 (2H, d), 8.1 (1H, t), 7.8–7.0 (16H, m), 4.7 (3H, m), 3.5–2.9 (2H, m).

The compound was further characterised and tested as the di-N-methyl-D-glucamine salt found: C, 56.99, H, 6.53; N, 6.69. $C_{50}H_{63}N_5O_{17}$. 2.6H$_2$O requires C, 57.03; H, 6.53; N, 6.65%

EXAMPLE 7

Preparation of (1R-(3,5-dicarboxyphenylaminocarbonyl)-2-phenylethylaminocarbonyl)-2-(cycloheptanemethylaminocarbonyl)-benzene The material was prepared essentially as in example 1 except that cycloheptanemethylamine was used in step e instead of 1-adamantanemethylamine. $^1$H NMR (d$^6$-DMSO) 67 13.4 (2H, br s), 10.2 (1H, s), 8.9 (1H, d), 8.7 (2H, d), 8.6 (1H, t), 8.2 (1H,t), 7.7–6.9 (9H, m), 4.8 (1H, m), 3.0–2.6 (4H, m), 2.0–1.0 (13H, m).

The compound was further characterised and tested as the di-N-methyl-D-glucamine salt found: C, 53.87; H, 7.34; N, 6.85. $C_{47}H_{69}N_5O_{17}$. 3.8H$_2$O requires C, 54.02; H, 7.39; N, 6.70%

EXAMPLE 8

Preparation of (1S-(3,5-dicarboxyphenylaminocarbonyl)-2-phenylethylaminocarbonylmethyl)-2-(1-adamantanemethylamino-carbonyl)benzene The material was prepared essentially as in example 1 except that homophthalic anhydride was used in step e instead of phthalic anhydride. $^1$H NMR (d$^6$-DMSO) δ 13.2 (2H, s), 10.4 (1H, s), 9.5 (1H, d), 8.7 (2H, s), 8.5 (2H, d), 8.2 (2H, m), 7.3 (9H, m), 4.8 (1H, m), 3.6 (2H, q), 3.3–2.7 (4H, m), 1.8 (3H, s), 1.5 (6H, q), 1.3 (6H, s).

EXAMPLE 9

Preparation of (1S-(3,5-dicarboxyphenylaminocarbonyl)-2-phenylethylaminocarbonyl)-2-(1-adamantanemethylaminocarbonyl-methyl)benzene The material was prepared following procedures analogous to those described in example 1. Homophthalic anhydride was opened with 1S-(3,5-dibenzyloxycarbonyl-phenylaminocarbonyl)-2-phenylethylamine and the resultant acid was coupled with 1-adamantanemethylamine using PyBROP. The correct regioisomer was isolated by column chromatography prior to hydrogenolysis to give the title compound. $^1$H NMR (d$^6$-DMSO) δ 13.3 (2H, br s), 10.4 (1H, s), 8.7 (1H, d), 8.5 (1H, t), 8.4 (2H, d), 8.2 (1H, t), 7.2 (9H, m), 4.6 (1H, m), 3.6 (2H, q), 3.3–2.9 (4H, m), 1.8 (3H, s), 1.6 (6H, q), 1.4 (6H, s).

The compound was further characterised and tested as the di-N-methyl-D-glucamine salt found: C, 56.45; H, 7.29; N, 6.77. $C_{51}H_{73}N_5O_{17}$. 2.9 H$_2$O. requires C, 56.74 H, 7.35; N, 6.49%

EXAMPLE 10

Preparation of 2-(1S-(3,5-dicarboxyphenylamino-carbonyl)-2-phenylethylaminocarbonyl)-3-(1-adamantanemethylamino-carbonyl)pyridine The compound was prepared essentially as in example 1 except that pyridine-2,3-dicarboxylic anhydride was used in step e instead of phthalic anhydride. 1H NMR (d$^6$-DMSO) δ 10.4 (1H, s), 8.8 (1H, m), 8.6 (1H, m) 8.5 (2H, s), 8.2 (1H, s), 8.2–7.0 (8H, m), 4.8 (1H, m), 3.3–2.8 (4H, m), 1.8 (3H, s), 1.6 (6H, q), 1.4 (6H, s).

The compound was further characterised and tested as the di-N-methyl-D-glucamine salt found: C, 54.59; H, 7.16; N, 7.83. $C_{49}H_{70}N_6O_{17}$. 3.5 H$_2$O. requires C, 54.62, H, 7.20; N, 7.80%

EXAMPLE 11

Preparation of 3-(1S-(3,5-dicarboxyphenylamino-carbonyl)-2-phenylethylaminocarbonyl)-4-(1-adamantanemethyl-aminocarbonyl)pyridine (and its regioisomer with arms reversed)

The compounds were prepared as a 1:1 mixture of regioisomers essentially as in example 1 except that pyridine-3,4-dicarboxylic anhydride was used in step e instead of phthalic anhydride. $^1$H NMR (d$^6$-DMSO) δ 10.4–6.4 (14H, m), 4.7 (1H, m), 3.3–2.6 (4H, m), 1.8 (3H, s), 1.5 (6H, q), 1.4 (6H, s).

EXAMPLE 12

Preparation of 3-(1S-(3,5-dicarboxyphenylamino-carbonyl)-2-phenylethylaminocarbonyl)-4-(1-adamantanemethyl-aminocarbonyl)furan a. 3-(1-adamantanemethylaminocarbonyl)furan carboxylic acid Dimethyl furan-3,4-dicarboxylate (prepared as described in Tetrahedron 1968, 24, 4501) was hydrolysed to the corresponding half acid half ester on treatment with one equivalent of sodium hydroxide in aqueous methanol at room temperature. This was coupled with 1-adamantanemethylamine using PyBROP following the procedure outlined in example 1 step f. The methyl ester was hydrolysed with methanolic sodium hydroxide to give the title compound.

b. (1S-(3,5-diallylyloxycarbonylphenylaminocarbonyl)-2-phenyl-ethylaminocarbonyl)-2-(1-adamantanemethylaminocarbonyl)furan 1S-(3,5-allyloxycarbonylphenylaminocarbonyl)-2-phenylethylamine was prepared essentially as in example 1 steps a–d except that allyl alcohol was used in place of benzyl alcohol in step a. This was coupled with the product of this example step a using PyBROP to give the title compound.

c. 3-(1S-(3,5-dicarboxyphenylaminocarbonyl)-2-phenylethylamino-carbonyl)-4-(1-adamantanemethylaminocarbonyl)furan Bis diethylammonium salt (1S-(3,5-diallylyloxycarbonylphenylaminocarbonyl)-2-phenyl-ethylaminocarbonyl)-2-(1-adamantanemethylaminocarbonyl)furan (250 mg, 0.36 mmol) was dissolved in dry THF (20 ml) under argon. Diethylamine (373 mg, 3.6 mmol) was added followed by tetrakis triphenylphosphinepalladium (42 mg, 0.036 mmol). After stirring at room temperature for 1 h the solution was decanted from a white precipitate and evaporated to yield the title compound as the bis diethylammonium salt. $^1$H NMR (d$^6$-DMSO) δ 10.5 (1H, br s), 10.0 (1H, br m), 9.3 (1H, br), 8.5–8.1 (5H, m), 7.4–7.1 (5H, m), 4.7 (1H, m), 3.2–2.8 (4H, m), 2.8 (4H, m), 1.9–1.5 (15H, m), 1.2 (6H, m). Found C, 63.29; H, 7.70; N, 8.77. $C_{42}H_{57}N_5O_8$.2H$_2$O requires C, 63.37; H, 7.70; N, 8.80%.

EXAMPLE 13

Preparation of 3-(1S-(3,5-dicarboxyphenylamino-carbonyl)-2-phenylethylaminocarbonyl)-4-(1-adamantanemethylamino-carbonyl)pyrrole The compound was prepared essentially as in example 12 except that dimethyl pyrrole-3,4-dicarboxylate was used in step a instead of dimethyl furan-3,4-dicarboxylate and that the dibenzyl ester was prepared and hydrogenolysed as described in example 1 step g to give the title compound as the free dicarboxylic acid 13.0 (2H, br s), 11.6 (1H, s), 10.5 (1H, s), 9.7 (1 h, d), 9.2 (1H, t), 8.4 (2H, s), 8.2 (1H, s), 7.4–7.1 (7H, m), 4.7 (1H. m), 3.2–2.9 (4H, m), 1.6 (3H, s), 1.5 (6H, m), 1.4 (6H, s).

The compound was further characterised and tested as the di-N-methyl-D-glucamine salt found: C, 52.18; H, 7.26; N, 7.16. $C_{48}H_{70}N_6O_{17}$. 6.1$H_2O$. requires C, 51.79, H, 7.45; N, 7.55%

EXAMPLE 14

Preparation of 1-(1S-(3,5-dicarboxyphenylamino-carbonyl)-2-phenylethylaminocarbonyl)-2-(1-adamantanemethyl-aminocarbonyl)-4-nitrobenzene a. 1S-(3,5-dimethyloxycarbonylphenylaminocarbonyl)-2-phenylethyl-amine 5-Aminophthalic acid was converted to the dimethyl ester on heating under reflux in acidified methanol. This was then coupled to BOC-L-phenylalanine and the BOC group removed following the procedures described in example 1 steps c and d to afford the title compound.

b. 2-(1S-(3,5-dimethyloxycarbonylphenylaminocarbonyl)-2-phenyl-ethylaminocarbonyl)-5-nitrobenzoic acid and 4-nitro regioisomer.

A solution containing the amine produced in step a (576 mg, 1.6 mmol) and 4-nitrophthalic anhydride (312 mg, 1.6 mmol) in acetonitrile (15 ml) was heated under reflux for 1.5 h. The mixture was cooled and allowed to stand at 5° C. for 2 h. The resultant white crystals were filtered and dried to afford the title compounds as a mixture of regioisomers (790 mg).

c. 1-(1S-(3,5-dimethyloxycarbonylphenylaminocarbonyl)-2-phenyl-ethylaminocarbonyl)-2-(1-adamantanemethylaminocarbonyl)-4-nitro benzene The mixture of acids produced in step b was coupled with 1-adamantanemethylamine using PyBROP following the procedure described in example 1 step f. The regioisomeric products were separated by column chromatography (silica, 80% dichloromethane, 20% ethyl acetate).

d. 1-(1S-(3,5-dicarboxyphenylaminocarbonyl)-2-phenylethylamino-carbonyl)-2-(1-adamantanemethylaminocarbonyl)-4-nitrobenzene.

The less polar regioisomer from step c (270 mg, 0.39 mmol) was dissolved in dioxan (12 ml). A solution of lithium hydroxide (42 mg, 1.19 mmol) in water (3 ml) was added and the mixture was stirred at room temperature for 4 h. The solvent was partially evaporated and the residue was poured into 10% aqueous citric acid (15 ml). The resultant white precipitate was filtered, washed with water, and dried to afford the title compound (223 mg). $^1$H NMR (d$^6$-DMSO) δ 13.3 (2H, s), 10.1 (1H, s), 9.2 (1H, d), 8.8 (1H, t), 8.6 (2H, s), 8.4 (1H, s), 8.3 (1H, d), 8.2 (1H, s), 7.4 (4H, s), 7.2 (1H, m), 4.8 (1H, m), 3.4 (1H, dd), 3.1 (1H, m), 2.9 (2H, m), 1.8–1.4 (15H, m).

EXAMPLE 15

Preparation of 1-(1S-(3,5-dicarboxyphenylamino-carbonyl)-2-phenylethylaminocarbonyl)-2-(1-adamantanemethyl-aminocarbonyl)-5-nitrobenzene This was prepared essentially as in example 14 except that the more polar regiosomer isolated from step c was converted to the title compound. $^1$H NMR (d$^6$-DMSO) δ 10.1 (1H, s), 9.2 (1H, d), 8.7 (1H, t), 8.6 (2H, s), 8.4 (1H, d), 8.2 (1H, s), 7.8 (1H, d), 7.8 (1H, s), 7.3 (5H, m), 4.8 (1H, m), 3.0 (4H, m), 2.0–1.4 (15H, m).

The compound was further characterised and tested as the di-N-methyl-D-glucamine salt found: C, 52.21; H, 6.91; N, 7.18. $C_{50}H_{70}N_6O_{19}$. 5.1 $H_2O$. requires C, 52.16, H, 7.02; N, 7.30%

EXAMPLE 16

Preparation of 1-(1S-(3,5-dicarboxyphenylamino-carbonyl)-2-phenylethylaminocarbonyl)-2-(1-adamantanemethyl-25 aminocarbonyl)-4-aminobenzene 1-(1S-(3,5-dibenzyloxycarbonylphenylaminocarbonyl)-2-phenyl-ethylaminocarbonyl)-2-(1-adamantanemethylaminocarbonyl)-4-nitro-benzene was prepared essentially as in example 14 steps b and c except that 1S-(3,5-dibenzyloxycarbonylphenylaminocarbonyl)-2-phenylethylamine was used instead of 1S-(3,5-dimethyloxy-carbonylphenylaminocarbonyl)-2-phenylethylamine. The less polar regioisomer was separated by column chromatography and hydrogenolysed following the procedure described in example 1 step g to give the title compound. 1H NMR (d$^6$-DMSO) δ 13.2 (2H, br s), 10.4 (1H, s), 8.8 (1H, d), 8.7 (2H, s), 8.2 (2H, m), 7.6 (1H, d), 7.3 (5H, m), 6.7 (1H, d), 6.3 (1H, s), 4.8–4.5 (3H, m), 3.4 (1H, m), 2.9 (3H, m), 1.8–1.3 (15H, m).

EXAMPLE 17

Preparation of 1-(1S-(3,5-dicarboxyphenylamino-carbonyl)-2-phenylethylaminocarbonyl)-2-(1-adamantanemethyl-aminocarbonyl)-5-aminobenzene This was prepared essentially as in example 16 except that the more polar regioisomer was converted to the title compound. 1H NMR (d6-DMSO) δ 10.2 (1H, s), 8.6 (2H, s), 8.5 (1H, d), 8.2 (2H, m), 7.2 (5H, m), 7.0 (1H, d), 6.7 (1H, s), 6.5 (1H, d), 4.7 (1H, m), 3.5–2.7 (4H, m), 1.8 (3H, br s), 1.6 (6H, m), 1.4 (6H, s).

EXAMPLE 18

Preparation of 1-(1S-(3,5-dicarboxyphenylamino-carbonyl)-2-phenylethylaminocarbonyl)-2-(1-adamantanemethyl-aminocarbonyl)-4-methoxybenzene This was prepared essentially as in example 1 except that 4-methoxyphthalic anhydride was used in step e in place of phthalic anhydride. A mixture of regioisomers was obtained which was separated by column chromatography after step f. The more polar regioisomer was converted to the title compound. 1H NMR (d$^6$-DMSO) δ 13.2 (2H, br s), 10.1 (1H, s), 8.8 (1H, d), 8.7 (2H, s), 8.4 (1H, t), 8.2 (1H, s), 7.3 (4H, m), 7.2 (1H, m), 7.1 (1H, d), 7.05 (1H, dd), 7.0 (1H, d), 4.7 (1H, m), 3.8 (3H, s), 3.3 (2H, m), 2.9 (2H, m), 1.8 (3H, s), 1.5 (6H, m), 1.4 (6H, s).

The compound was further characterised and tested as the di-N-methyl-D-glucamine salt found: C, 55.41; H, 7.43; N, 6.52. $C_{51}H_{73}N_5O_{18}$. 3.2 $H_2O$. requires C, 55.58, H, 7.27; N, 6.35%

EXAMPLE 19

Preparation of 1-(1S-(3,5-dicarboxyphenylamino-carbonyl)-2-phenylethylaminocarbonyl)-2-(1-adamantanemethyl-aminocarbonyl)-5-methoxybenzene This was prepared essentially as in example 18 except that the less polar regioisomer from step f was converted to the title compound. $^1$H NMR (d$^6$-DMSO) δ 14.2 (2H, br s), 10.1 (1H, s), 8.8 (1H, d), 8.7 (2H, s), 8.4 (1H, t), 8.2 (1H, s), 7.7 (1H, d), 7.3 (4H, m), 7.3 (1H, m), 7.0 (1H, dd), 6.3 (1H, d), 4.7 (1H, m), 3.8 (3H, s), 3.5 (1H, dd), 3.2 (1H, dd), 2.9 (2H, m), 1.8 (3H, m), 1.5 (6H, m), 1.4 (6H, S).

The compound was further characterised and tested as the di-N-methyl-D-glucamine salt found: C, 5 6.62; H, 7.14; N, 6.36. $C_{51}H_{73}N_5O_{18}$. requires C, 56.59 H, 7.19; N, 6.47%

EXAMPLE 20

Preparation of 1-(1S-(3,5-dicarboxyphenylamino-carbonyl)-2-phenylethylaminocarbonyl)-2-(1-adamantanemethyl-aminocarbonyl)-4-acetamidobenzene (and its regioisomer with arms reversed)

This was prepared essentially as in example 1 except that 4-acetamidophthalic anhydride was used in step e in place of phthalic anhydride. A mixture of regioisomers was obtained which was not separated. 1H NMR (d$^6$-DMSO) δ 10.2 (2H, m), 8.9–8.1 (5H, m), 7.7–7.5(2H, m), 7.4–7.0 (6H, m), 4.7 (1H, m), 3.4 (1H, m), 2.9 (3H, m), 2.1 (2x s, 3H), 1.8 (3H, s), 1.5 (6H, m), 1.4 (6H, s).

The compound was further characterised and tested as the N-methyl-D-glucamine salt found: C, 59.00; H, 6.82; N, 7.66. $C_{51}H_{73}N_5O_{18}$. 2.1 $H_2O$. requires C, 56.59 H, 7.19; N, 6.47%

EXAMPLE 21

Preparation of 1-(1S-(3,5-dicarboxyphenylamino-carbonyl)-2-phenylethylaminocarbonyl)-2-(1-adamantanemethyl-aminocarbonyl)-4-acetoxybenzene (and its regioisomer with arms reversed)

This was prepared essentially as in example 1 except that 4-acetoxyphthalic anhydride was used in step e in place of phthalic anhydride. A mixture of regioisomers was obtained which was not separated. $^1$H NMR (d$^6$-DMSO) δ 10.2 (1H, 2x s), 8.89–8.2 (5H, m), 7.6–6.4 (8H, m), 4.7 (1H, m), 3.2–2.8 (4H, m), 2.0–1.4 (18H, m).

The compound was further characterised and tested as the N-methyl-D-glucamine salt found: C, 58.94; H, 6.69; N, 6.27. $C_{45}H_{56}N_4O_{14}$. 2.1 $H_2O$. requires C, 59.08, H, 6.63; N, 6.12%

EXAMPLE 22

Preparation of 1-(1S-(3,5-dicarboxyphenylamino-carbonyl)-2-phenylethylaminocarbonyl)-2-(1-adamantanemethyl-aminocarbonyl)-3,6-difluorobenzene This was prepared essentially as in example 1 except that 3,6-difluorophthalic anhydride was used in step e in place of phthalic anhydride. $^1$H NMR (d$^6$-DMSO) δ 10.0 (1H, s), 9.2 (1H, d), 8.6 (3H, m), 8.2 (1H, s), 7.3 (7H, m), 4.8 (1H, m), 3.3 (1H, m), 2.9 (3H, m), 1.8 (3H, m), 1.6–1.3 (12H, m).

The compound was further characterised and tested as the di-N-methyl-D-glucamine salt found C, 54.28; H, 6.72; N, 6.32. $C_{50}H_{69}N_5O_{17}.F_2$.3.0 $H_2O$. requires C, 54.41, H, 6.85; N, 6.34%.

EXAMPLE 23

Preparation of 1-(1S-(3,5-dicarboxyphenylamino-carbonyl)-2-phenylethylaminocarbonyl)-2-(1-adamantanemethylamino-carbonyl)-5-hydroxybenzene This was prepared essentially as in example 1 except that 4-hydroxyphthalic anhydride was used in step e in place of phthalic anhydride. $^1$H NMR (d$^6$-DMSO) δ 13.2 (2H, br s), 10.3 (1H, s), 10.1 (1H, s), 8.8 (1H, d), 8.7 (2H, s), 8.4 (1H, m), 8.3 (1H, t), 8.2 (1H, s), 7.6 (1H, d), 7.3 (4H, m), 6.8 (1H, dd), 6.4 (1H, d), 4.7 (1H, m), 3.1 (1H, m), 2.9 (3H, m), 1.8 (3H, s), 1.5 (6H, m), 1.4 (6H, s).

The compound was further characterised and tested as the di-N-methyl-D-glucamine salt found: C, 56.71; H, 6.99; N, 6.59. $C_{50}H_{71}N_5O_{18}$.1.5$H_2O$. requires C, 56.78, H, 7.06; N, 6.62%.

EXAMPLE 24

Preparation of 1-(1S-(3,5-dicarboxyphenylamino-carbonyl)-2-phenylethylaminocarbonyl)-2-(1-adamantanemethyl-aminocarbonyl)-4-methylaminobenzene a. 1-(1S-(3,5-dimethyloxycarbonylphenylaminocarbonyl)-2-phenylethylaminocarbonyl)-2-(1-adamantanemethylaminocarbonyl)-4-methylaminobenzene The less polar regioisomer obtained from example 14 step c was hydrogenolysed following the procedure described in example 1 step g. The resultant amine (0.5 g, 0.7 mmol) was treated with iodomethane (0.28 ml, 4.4 mmol) and diiso-propylethylamine (0.7 ml, 3.7 mmol) in DMF (5 ml) at room temperature for 48 h. The mixture was concentrated in vacuo and the residue was taken up in ethyl acetate and washed with 1M hydrochloric acid then saturated sodium hydrogen-carbonate solution, dried ($Na_2SO_4$) and evaporated. The crude mixture was separated by column chromatography (silica, ethyl acetate/dichloromethane 1:1). to yield the title compound (0.10 g) and the corresponding dimethylated compound (0.16 g).

b. 1-(1S-(3,5-dicarboxyphenylaminocarbonyl)-2-phenylethylamino-carbonyl)-2-(1-adamantanemethylaminocarbonyl)-4-methylaminobenzene.

The more polar compound obtained from step a was hydrolysed with lithium hydroxide in aqueous dioxan following the procedure described in example 14 step d to give the title compound. $^1$H NMR (d$^6$-DMSO) δ 13.0 (2H, br s), 10.2 (1H, s), 8.6 (2H, s), 8.5 (1H, d), 8.2 (1H, t), 8.1 (1H, s), 7.3 (5H, m), 7.0 (1H, d), 6.7 (1H, s), 6.5 (1H, d), 6.2 (1H, br s), 4.7 (1H, m), 2.9 (4H, m), 2.7 (3H, s), 1.8 (3H, s), 1.6–1.4 (12H, m).

EXAMPLE 25

Preparation of 1-(1S-(3,5-dicarboxyphenylamino-carbonyl)-2-phenylethylaminocarbonyl)-2-(l-adamantanemethyl-aminocarbonyl)-4-dimethylaminobenzene The compound was prepared essentially as in example 24 except that the less polar product of step a was converted to the title compound. $^1$H NMR (d$^6$-DMSO) δ 10.3 (3H, s), 8.7–8.1 (5H, m), 7.3 (5H, m), 7.1–6 (3H, m), 4.7 (1H, m), 3.0 (4H, m), 2.9 (6H, s), 1.8 (3H, s), 1.6–1.2 (12H, m).

EXAMPLE 26

Preparation of 7-(1S-(3,5-dicarboxyphenylamino-carbonyl)-2-phenylethylaminocarbonyl)-2-(1-adamantanemethyl)indol-1-one a. Dimethyl 3-Bromomethylphthalate Azo-isobutyronitrile (200 mg) was added to a solution of dimethyl phthalate (4.5 g, 21.6 mmol) in carbon tetrachloride containing N-bromosuccinimide (3.8 g, 21.6 mmol). The mixture was heated under reflux for 4 h when all the N-bromosuccinimide had been consumed. The succinimide was removed by filtration and the filtrate was evaporated to give the title compound (6.0 g) which was used without further purification.

b. Methyl 2-(1-adamantanemethyl) indol-1-one-7-carboxylate

To a stirred solution of 1-adamantanemethylamine (0.85 g, 5.2 mmol) and diisopropylethylamine (0.9 ml, 5.2 mmol) in THF (8 ml) was added a solution of the bromide from step a (1.4 g, 5.0 mmol) in THF (6 ml ) dropwise over 15 minutes. The mixture was stirred at room temperature for a further 1.5 h and the resultant white precipitate (1-adamantanemethylamine hydrogen bromide) was removed by filtration. The filtrate was diluted with ethyl acetate then washed sequentially with 10% aqueous citric acid, saturated sodium hydrogencarbonate solution, water, and brine, dried and concentrated to a small volume. Diethyl ether was added and the resultant precipitate was filtered, washed with a further portion of ether and dried to afford the title compound (0.74 g).

c. 2-(1-Adamantanemethyl) indol-1-one-7-carboxylic acid

A solution of the methyl ester from step b (0.6 g, 1.9 mmol) and potassium hydroxide (0.2 g, 3.6 mmol) in propan-2-ol (30 ml ) and water (3 ml) was heated under reflux for 2 h. The mixture was concentrated in vacuo and the residue poured into 10% citric acid solution (30 ml. The resultant precipitate was filtered, washed with water, and dried to yield the title compound (0.47 g).

d. 7-(1S-(3,5-dibenzyloxycarbonylphenylaminocarbonyl)-2-phenyl-ethylaminocarbonyl)-2-(1-adamantanemethyl)indol-1-one.

Oxalyl chloride (0.07 ml, 0.8 mmol) then DMF (4 drops) were added dropwise to a solution of the acid from step c (0.2 g, 0.6 mmol) in dry dichloromethane (20 ml). The yellow solution was stirred at room temperature for 0. 5 h then evaporated to dryness. The residue was redissolved in dichloromethane (20 ml) and triethylamine (0.1 ml, 0.7 mmol) and 1S-(3,5-dibenzyloxycarbonylphenylaminocarbonyl)-2-phenylethyl amine (0.3 g, 0.6 mmol) were added. The mixture was stirred at room temperature for 72 h then washed sequentially with 10% aqueous citric acid, saturated sodium hydrogencarbonate solution, water, and brine, dried and evaporated. The crude product was purified by column chromatography (silica, 15% ethyl acetate, 85% dichloromethane) yielding the title compound (363 mg, 72%).

e. 7-(1S-(3,5-dicarboxyphenylaminocarbonyl)-2-phenylethylamino-carbonyl)-2-(1-adamantanemethyl)indol-1-one The product from step d was hydrogenolysed using the procedure described in example 1, step g to give the title compound. $^1$H NMR ($d^6$-DMSO) δ 10.9 (1H, d), 10.7 (1H, s), 8.6 (2H, s), 8.2 (1H, s), 7.7 (3H, m), 7.3 (2H, m), 7.2 (3H, m), 4.8 (1H, m), 4.7 (2H, s), 3.6–2.9 (4H, m), 1.9 (3H, s), 1.6 (12H, s).

The compound was further characterised and tested as the di-N-methyl-D-glucamine salt found: C, 55.65; H, 7.21; N, 6.05. $C_{51}H_{71}N_5O_{17}$ 4.4 $H_2O$. requires C, 55.45; H, 7.27; N, 6.34%.

EXAMPLE 27

Preparation of 7-(1-adamantanemethylaminocarbonyl)-2-(1S-(3,5-dicarboxyphenylaminocarbonyl)-2-phenylethyl) indol-1-one This was prepared essentially as in example 26 except that di methyl-bromomethylphthalate was reacted with 1S-(3,5-dibenzyloxycarbonylphenylaminocarbonyl)-2-phenylethyl amine following the procedure given in step b above. Hydrolysis of the methyl ester with lithium hydroxide in aqueous dioxan was followed by coupling to 1-adamantanemethylamine using oxalyl chloride and hydrogenolysis of the benzyl esters using the methods outlined in steps d and e above. $^1$H NMR (d6-DMSO) δ 10.9 (1H, t), 10.7 (1H, s), 8.4 (2H, s), 8.2 (1H, m), 8.1 (1H, s), 7.7 (2H, m), 7.3 (2H, m), 7.2 (3H, m), 5.3 (1H, m), 4.7 (2H, q), 3.5–3.2 (2H, m), 3.1 (1H, dd), 3.0 (1H, dd), 1.9 (3H, s), 1.6 (6H, q), 1.5 (6H, s).

The compound was further characterised and tested as the di-N-methyl-D-glucamine salt found: C, 56.68; H, 7.53; N, 6.30. $C_{51}H_{71}N_5O_{17}$ 3.1 $H_2O$. requires C, 56.64; H, 7.19; N, 6.48%.

EXAMPLE 28

Preparation of 1-(1S-(3,5-dicarboxyphenylaminocarbonyl)-2-(2-fluorophenyl) ethylaminocarbonyl)-2-(1-adamantane-methylaminocarbonyl)-4-methoxybenzene This was prepared essentially as in example 18 except that BOC-L-2-fluorophenylalanine was used in step c in place of BOC-L-phenylalanine. $^1$H NMR ($d^6$-DMSO) δ 13.0 (2H, br s), 10.1 (1H, s), 8.8 (1H, d), 8.6 (2H, s), 8.5 and 8.1 (1H, 2 x t), 8.2 (1H, s), 7.3 (7H, m), 4.8 (1H, m), 3.8 (3H, s), 3.5 (1H, m), 3.0 (3H, m), 1.9 and 1.8 (3H, 2 x s), 1.5 (12H, m).

The compound was further characterised and tested as the di-N-methyl-D-glucamine salt

EXAMPLE 29

Preparation of 1-(1S-(3,5-dicarboxyphenylaminocarbonyl)-2-(2-fluorophenyl)ethylaminocarbonyl)-2-(1-adamantane-methylaminocarbonyl)-5-methoxybenzene This was prepared essentially as in example 19 except that BOC-L-2-fluorophenylalanine was used in step c in place of BOC-L-phenylalanine. $^1$H NMR ($d^6$-DMSO) δ 13.2 (2H, br s), 10.2 (1H, s), 9.0 (1H, d), 8.7 (2H, s), 8.4 (1H, t), 8.2 (1H, s), 7.7 (1H, m), 7.3 (2H, m), 7.2 (2H, m), 7.0 (1H, d), 6.3 (1H, s), 4.8 (1H, m), 3.6 (1H, m), 3.0 (3H, m), 1.8 (3H, s), 1.5 (12H, m).

The compound was further characterised and tested as the di-N-methyl-D-glucamine salt

EXAMPLE 30

Preparation of 1-(1S-(3,5-dicarboxyphenylaminocarbonyl)-2-phenylethylaminocarbonyl)-2-(1-adamantanemethyl-aminocarbonyl)-4-phenylbenzene and regioisomer with arms reversed This was prepared essentially as in example 1 except that 4-phenylphthalic anhydride was used in step e in place of phthalic anhydride. This was prepared from ethyl 2-cyano-5-phenylbenzoate by exhaustive hydrolysis (to the diacid), followed by heating to give the anhydride. The ethyl 2-cyano-5-phenylbenzoate was prepared in several steps from 4-bromoanthranilic acid as shown in J. Med. Chem. 1992, 35, 4613.

The compound was further characterised and tested as the di-N-methyl-D-glucamine salt The compounds of the examples were tested for binding at the $CCK_B$ receptor in mouse cortical membranes by means of a radioligand binding assay. The procedure was as follows:

The whole brains from male mice (CD1 22–25 g; Charles River) were removed and placed in ice-cold buffer (pH7.2@21±3° C.) of the following composition (mM); 10 HEPES, 130 NaCl, 4.7 KCl, 5 $MgCl_2$, 1 EDTA and containing 0.25 g.l$^{-1}$ bacitracin. The cortex was dissected, weighed and homogenised in 40 ml ice-cold buffer using a Teflon-in-glass homogeniser. The homogenate was centrifuged at 39,800 g for 20 min at 4° C., the supernatant discarded and the pellet resuspended by homogenisation in fresh buffer. The homogenate was recentrifuged (39,800 g; 20 min@4° C.) and the final pellet was resuspended in HEPES buffer to give a tissue concentration of 2 mg.ml$^{-1}$ (original wet weight).

The membranes (400 ml) were incubated for 150 min at 21±3° C. in a final volume of 0.5 ml with HEPES buffer containing [$^{125}$I]-CCK8S (0.05 ml; 200 pM NEN 2200 Ci.mmol$^{-1}$) and competing compound. Total and non-specific binding of [$^{125}$I]-CCK8S were defined using 0.05 ml of buffer and 0.05 ml of 10 mM L-365,260, respectively. The assay was terminated by rapid filtration through pre-soaked Whatman GF/B 35 filters using a Brandell Cell harvester. The filters were washed (3×3 ml) with ice-cold 5 mM Tris-HCl (pH7.4@4° C.) and bound radioactivity determined by counting (1 min.) in a gamma-counter.

The results obtained from the $CCK_8$ assays are set out in Table 1.

TABLE 1

| Example | $CCK_B$ p$K_i$ |
|---------|---------------|
| 1 | 7.1 |
| 2 | 5.9 |
| 3 | 6.4 |
| 4 | 7.0 |
| 5 | 6.3 |
| 6 | 6.3 |
| 7 | 6.5 |
| 8 | 6.8 |
| 9 | 6.6 |
| 10 | 6.1 |
| 11 | 7.2 |
| 12 | 6.3 |
| 13 | 7.2 |
| 14 | 6.3 |
| 15 | 6.0 |
| 16 | 6.7 |
| 17 | 7.3 |
| 18 | 7.6 |
| 19 | 6.8 |
| 20 | 6.3 |
| 21 | 6.7 |
| 22 | 7.3 |
| 23 | 6.5 |
| 24 | 8.1 |
| 25 | 8.8 |
| 26 | 7.0 |
| 27 | 6.9 |
| 28 | 7.8 |
| 29 | 7.8 |

The compounds of the examples were also tested for gastrin antagonist activity in an immature rat stomach assay. The procedure was follows:

The oesophagus of immature rats (33–50 g, ca. 21 days old) was ligated at the level of the cardiac sphincter and the duodenal sphincter was cannulated. The stomach was excised and flushed with ca. 1 ml unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3\times10^{-8}$ M5methylfurmethide, maintained at 37° and gassed vigorously with 95% $O_2$/5% $CO_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et. al., Br. J. Pharmacol., 1985, 86, 581.

The results obtained from the gastrin assays are set out in Table 2.

TABLE 2

| Example | Gastrin p$K_B$ |
|---------|----------------|
| 1 | 8.4 |
| 2 | 7.6 |
| 3 | 7.8 |
| 4 | 7.7 |
| 6 | 6.1 |
| 7 | 6.3 |
| 10 | 7.4 |
| 12 | 6.5 |
| 13 | 7.6 |
| 14 | 7.0 |
| 15 | 6.5 |
| 16 | 7.2 |
| 17 | 7.7 |
| 18 | 7.5 |
| 19 | 7.9 |
| 21 | 7.3 |
| 22 | 7.5 |
| 23 | 6.9 |
| 24 | 8.3 |
| 25 | 8.6 |
| 26 | 7.2 |
| 28 | 7.9 |
| 29 | 5.8 |

The compounds of the examples were also tested in a $CCK_A$ binding assay as follows:

The pancreatata were removed from male guinea-pigs (200–300 g; Dunkin Hartley) and placed in ice-cold HEPES buffer (pH 7.2@21 ±3° C.). The pancreatata were homogenised in 40 ml ice-cold HEPES buffer using a polytron (Brinkman, PT10, setting 10) 4×1 second. The homogenate was centrifuged at 39,800 g for 15 min at 4° C. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original wet weight), and filtered through 500 μm pore-size Nytex mesh.

The membranes (400 μl; containing 0.375 μM PD134, 308) are incubated for 150 minutes at 21±3° C. in a final volume of 0.5 ml with HEPES buffer containing [$^{125}$I]-$CCK_8$(S) (50 μl; 200 pM) and competing compound. Total and non-specific binding of [$^{125}$I]-CCK$^8$(S) are defined using 50 μl of buffer and 50 μl of 100 nM L-364, 718respectively. The assay is terminated by rapid filtration through pre-soaked Whatman GF/B filters using a Brandell Cell Harvester. The filters were washed (3×3 ml) with ice-cold 50 mM Tris HCl (pH 7.4 at 4° C. and bound radioactivity is determined by counting (1 min) in a gamma counter.

The results are set out in Table 3.

TABLE 3

| Example | CCK$_A$ pK$_i$ |
|---------|----------------|
| 1 | 5.5 |
| 2 | 5.8 |
| 3 | 5.1 |
| 4 | 5.3 |
| 5 | 7.0 |
| 6 | 6.3 |
| 7 | 5.9 |
| 8 | 5.5 |
| 9 | 5.5 |
| 10 | 5.7 |
| 11 | 5.1 |
| 12 | 5.2 |
| 13 | 5.7 |
| 14 | 5.5 |
| 15 | 6.0 |
| 16 | 5.4 |
| 17 | 4.9 |
| 19 | 5.7 |
| 20 | 5.7 |
| 21 | 5.3 |
| 26 | 5.5 |
| 27 | 5.5 |

We claim:

1. A compound of the formula

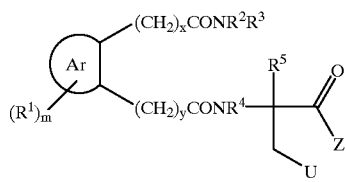

wherein

Ar is phenyl;

$R^1$ independently is selected from the group consisting of halo, amino, nitro, cyano, sulphamoyl, sulphonyl, trifluoromethyl, $C_1$ to $C_3$ alkyl, $C_1$ to $C_3$ alkylamino, $C_1$ to $C_3$ dialkylamino, phenyl, substituted phenyl, $C_1$ to $C_3$ alkoxy, hydroxy, esterified hydroxy, $C_1$ to $C_3$ hydroxyalkyl, $C_1$ to $C_3$ alkylcarboxyamino, carboxy, esterified carboxy and amidated carboxy;

m is 0, 1, 2, 3, or 4, provided that m is not more than 2 unless $R^1$ is exclusively halo;

x+y=0 or 1

$R^2$ and $R^4$ independently are H, or $C_1$ to $C_3$ alkyl;

$R^3$ is H or $C_1$ to $C_{15}$ hydrocarbyl, wherein one or more hydrogen atoms of the hydrocarbyl group may be replaced by a halogen atom, and wherein up to two of the carbon atoms may be replaced by a nitrogen, oxygen or sulphur atom, provided that $R^3$ does not contain a —O—O— group;

$R^5$ is H or $C_1$ to $C_3$ alkyl;

U is a cyclic moiety, selected from the group consisting of aryl, aromatic heterocyclic, non-aromatic heterocyclic, and cycloalkyl groups;

wherein said aryl or aromatic group contains up to 3 substituents selected from the group consisting of halo, amino, nitro, cyano, sulphamoyl, sulphonyl, trifluoromethyl, $C_1$ to $C_3$ alkyl, $C_1$ to $C_3$ alkylamino, $C_1$ to $C_3$ dialkylamino, phenyl, $C_1$ to $C_3$ alkoxy, hydroxy, esterified hydroxy, $C_1$ to $C_3$ hydroxyalkyl, $C_1$ to $C_3$ alkylcarboxyamino, carboxy, esterified carboxy and amidated carboxy;

wherein said heterocyclic group is selected from the group consisting of benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoguinolyl, naphthridinyl, cinnolinyl, quinazolinyl, pyridopyridyl, benzoxazinyl, quinoxadinyl, chromenyl, chromanyl, isochromanyl and carbolinyl;

Z is a group of the formula

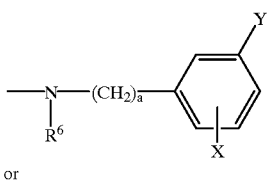

or

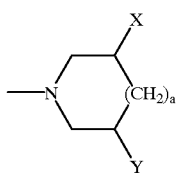

wherein $R^6$ is H or $C_1$ to $C_3$ alkyl;

X is —CO$_2$H, esterified carboxy, amidated carboxy, tetrazolyl, hydroxy, cyano, amidino, —CH$_2$OH, —SO$_2$NHCOR$^7$, —SONHCOR$^7$, —COR$^7$, —NHSO$_2$R$^7$, —CONHSO$_2$R$^7$, —NHCOR$^7$ or —SO$_2$NHR$^8$, wherein R$^7$ is $C_1$ to $C_6$ alkyl, $C_1$ to $C_6$, aryl or substituted aryl, and R$^8$ is —OH, —CN, $C_1$ to $C_6$ alkyl, $C_1$ to $C_6$ haloalkyl, aryl or substituted aryl;

Y is H or a group selected from those recited above for X; and a is 0, 1, or 2, or a pharmaceutically acceptable salt thereof.

2. A compound according to claim 1, wherein $R^3$ is $C_6$ to $C_8$ straight or branched chain alkyl or cycloalkyl, or $R^{12}$—(CH$_2$)$_p$—, wherein $R^{12}$ is selected from phenyl, 1-naphthyl, 2-naphthyl, indolyl, norbornyl, 1-adamantyl, 2-adamantyl, cyclohexyl or cycloheptyl, and p is from 0 to 3.

3. A compound according to claim 1, wherein m is from 0 to 2.

4. A compound according to claim 1, selected from the group consisting of
(1S-(3,5-dicarboxyphenylaminocarbonyl)-2-phenylethylaminocarbonyl)-2-(1-adamantanemethylaminocarbonyl)benzene,
(1S-(3,5-dicarboxyphenylaminocarbonyl)-2-(4-hydroxyphenyl)-ethylaminocarbonyl)-2-(1-adamantanemethyl-aminocarbonyl)-benzene,
(1R-(3,5-dicarboxyphenylaminocarbonyl)-2-phenylethylaminocarbonyl)-2-(1-adamantanemethylaminocarbonyl)-benzene,
(1R-(3,5-dicarboxyphenylaminocarbonyl)-2-(2-fluorophenyl)ethylaminocarbonyl)-2-(1-adamantanemethylamino-carbonyl)benzene,
(1R-(3,5-dicarboxyphenylaminocarbonyl)-2-phenylethylaminocarbonyl)-2-(1-naphthalenemethylaminocarbonyl)-benzene (1R-(3,5-dicarboxyphenylaminocarbonyl)-2-phenylethyl-aminocarbonyl)-2-(2-naphthalenemethylaminocarbonyl) benzene, (1R-(3,5-carbonylphenylaminocarbonyl) 2-phenylethylaminocarbonyl)-2-(cycloheptanemethylaminocarbonyl)benzene, (1S-(3,5-dicarboxyphenylaminocarbonyl)-2-phenylethylaminocarbonylmethyl)-2-(1-adamantanemethylaminocarbonyl)benzene, (1S-(3,5-dicarboxyphenylaminocarbonyl)-2-phenylethylaminocarbonyl)-2-(1-adamantanemethylaminocarbonylmethyl)benzene,

[2-(1S-(3,5-dicarboxyphenylaminocarbonyl)-2-phenylethylaminocarbonyl)-3-(1-adamantanemethylaminocarbonyl)pyridine, 3-(1S-(3,5-dicarboxyphenylaminocarbonyl)-2-phenylethylaminocarbonyl)-4-(1-adamantanemethylaminocarbonyl)pyridine or its regioisomer, 3-(1S-(3,5-dicarboxyphenylaminocarbonyl)-2-phenylethylaminocarbonyl)-4-(1-adamantanemethylaminocarbonyl)furan, 3-(1S-(3,5-dicarboxyphenylaminocarbonyl)-2-phenylethylaminocarbonyl)-4-(1-adamantanemethylaminocarbonyl)pyrrole,)]

1-(1S-(3,5-dicarboxyphenylaminocarbonyl)-2-phenylethylaminocarbonyl)-2-(1-adamantanemethylaminocarbonyl)-4-nitrobenzene, 1-(1S-(3,5-dicarboxyphenylaminocarbonyl)-2-phenylethylaminocarbonyl)-2-(1-adamantanemethylaminocarbonyl)-5-nitrobenzene, 1(1S-(3,5-dicarboxyphenylaminocarbonyl)-2-phenylethylaminocarbonyl)-2-(1-adamantanemethylaminocarbonyl)-4-aminobenzene, 1-(1S-(3,5-dicarboxyphenylaminocarbonyl)-2-phenylethylaminocarbonyl)-2-(1-adamantanemethylaminocarbonyl)-5-aminobenzene, 1-(1S-(3,5-dicarboxyphenylaminocarbonyl)-2-phenylethylaminocarbonyl)-2-(1-adamantanemethylaminocarbonyl)-4-methoxybenzene, 1-(1S-(3,5-dicarboxyphenylaminocarbonyl)-2-phenylethylaminocarbonyl)-2-(1-adamantanemethylaminocarbonyl)-5-methoxybenzene, 1-(1S-(3,5-dicarboxyphenylaminocarbonyl)-2-phenylethylaminocarbonyl)-2-(1adamantanemethylaminocarbonyl)-4-acetamidobenzene or its regioisomer, 1-(1S-(3,5-dicarboxyphenylaminocarbonyl)-2-phenylethylaminocarbonyl)-2-(1-adamantanemethylaminocarbonyl)-4-acetoxybenzene or its regioisomer, 1-(1S-(3,5-dicarboxyphenylaminocarbonyl)-2-phenylethylaminocarbonyl)-2-(1-adamantanemethylaminocarbonyl)-3,6-difluorobenzene, 1-(1S-(3,5-dicarboxyphenylaminocarbonyl)-2-phenylethylaminocarbonyl)-2-(1-adamantanemethylaminocarbonyl)-5-hydroxybenzene, 1-(1S-(3,5-dicarboxyphenylaminocarbonyl)-2-phenylethylaminocarbonyl)-2-(1-adamantanemethylaminocarbonyl)-4-methylaminobenzene, 1-(1S-(3,5-dicarboxyphenylaminocarbonyl)-2-phenylethylaminocarbonyl)-2-(1-adamantanemethylaminocarbonyl)-4-dimethylaminobenzene 1-(1S-(3,5-dicarboxyphenylaminocarbonyl)-2-(2-fluorophenyl)ethylaminocarbonyl)-2-(1-adamantanemethylaminocarbonyl)-4-methoxybenzene, 1-(1S-(3,5-dicarboxyphenylaminocarbonyl)-2-(2-fluorophenyl)ethylaminocarbonyl)-2-(1-adamantanemethylaminocarbonyl)-5-methoxybenzene, and 1-(1S-(3,5-dicarboxyphenylaminocarbonyl)-2-phenylethylaminocarbonyl)-2-(1-adamantanemethylaminocarbonyl)-4-phenylbenzene or its regioisomer.

5. A pharmaceutical composition comprising a compound according to claim 1, together with a pharmaceutically acceptable diluent or carrier.

6. A method of making a compound according to claim 1, said method including the step of reacting a compound of the formula

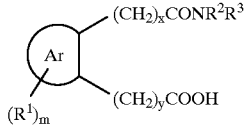

with a suitably protected compound of formula

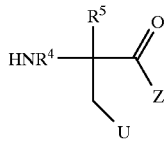

* * * * *